United States Patent [19]

Cooper et al.

[11] Patent Number: 4,923,476

[45] Date of Patent: May 8, 1990

[54] ALIGNMENT DEVICE AND METHOD OF ARTIFICIAL LIMB MANUFACTURE

[75] Inventors: John E. Cooper, Leatherhead; Alun Wilcox, Richmond, both of United Kingdom

[73] Assignee: J. E. Hanger & Company Limited (British Company), London, United Kingdom

[21] Appl. No.: 172,228

[22] Filed: Mar. 23, 1988

[30] Foreign Application Priority Data

Mar. 24, 1987 [GB] United Kingdom ............... 8706912

[51] Int. Cl.$^5$ .............................................. A61F 2/80
[52] U.S. Cl. ...................................................... 623/38
[58] Field of Search ................. 403/291, 223, 225, 50, 403/51, 280; 425/DIG. 45, 107, 112; 264/316, 261, 222; 249/55–117; 623/37–56, 17, 38

[56] References Cited

U.S. PATENT DOCUMENTS

| | | | |
|---|---|---|---|
| 2,424,542 | 7/1947 | Adams | 403/281 |
| 2,460,981 | 2/1949 | Francisco | 403/225 |
| 2,568,226 | 4/1951 | Drake | 403/51 |
| 3,132,479 | 5/1964 | Kuhn | 403/51 |
| 3,359,014 | 12/1967 | Clements | 403/50 |
| 4,378,935 | 4/1983 | Brown | 403/291 |
| 4,785,495 | 11/1988 | Dellis | 264/222 |

FOREIGN PATENT DOCUMENTS 268345  3/1926  United Kingdom .................. 403/50

*Primary Examiner*—Richard J. Apley
*Assistant Examiner*—James Prizant
*Attorney, Agent, or Firm*—Shoemaker and Mattare, Ltd.

[57] ABSTRACT

An alignment device is provided for an artificial limb and comprises first and second end plates fastenable to respective upper and lower parts of the limb in a predetermined angular and axial position. A flexible sleeve fastened between the end plates forms therewith an internal cavity for containing a body of settable fluid. When the fluid body is in a flowable state relative movement between upper and lower parts of the limb during alignment thereof are accommodated by flexion of the sleeve. When the fluid body is in a solidified state it establishes a rigid mechanical linkage between the end plates, thereby preventing relative movement of the upper and lower parts. Angular alignment between an end plate and an adjoining part of the limb is provided by pegs on one of said parts engaging sockets on the other of said parts. Radially flanged ends of the end plate and the adjoining part of the limb abut, and a releasable clamping band encircles the abutting flanges to hold said end plate and said adjoining part axially together. Cavity is air filled prior to use, and passages lead through at least one end plate to the internal cavity for introduction of hardenable material therein. Breather passages are provided for outflow of air from the cavity. The invention also provides a method for manufacturing an artificial limb, by fitting a temporary mechanical alignment device between a stump socket and lower parts of the limb, releasing a mechanism of the temporary alignment device, adjusting the relative positions of the stump socket and the lower parts in a jig, reclamping the alignment device and removing the limb from the jig so that the patient can test the limb. A permanent alignment device having the structure above described is fitted when the correct alignment has been obtained.

17 Claims, 3 Drawing Sheets

4,923,476

ALIGNMENT DEVICE AND METHOD OF ARTIFICIAL LIMB MANUFACTURE

FIELD OF THE INVENTION

This invention relates to an alignment device for an artificial limb and to a method for making an artificial limb using such a device.

SUMMARY OF THE INVENTION

Broadly stated, an alignment device for an artificial limb comprises first and second end plates, means for fastening each end plate to respective upper and lowre parts of the limb in a predetermined angular and axial position, and flexible sleeve means fastened between the end plates to define therewith an internal cavity for containing a body of settable fluid so that when the fluid body is in a flowable state relative movement between upper and lower portions of the limb during alignment thereof are accommodated by flexion of the sleeve and when the body is in a solidified state it establishes a rigid mechanical linkage between the end plates.

The invention further provides a method for manufacturing an artificial limb, comprising the steps of fitting between a stump socket and lower parts of the limb a temporary mechanical alignment device which can be loosened to enable adjustment of upper and lower parts of the limb by jig means and which can be releaseably clamped to preserve an alignment, releasing a mechanism of the temporary alignment device, adjusting the relative positions of the stump socket and the lower parts in the jig means, reclamping the alignment device and removing the limb from the jig means so that the patient can test the limb.

DESCRIPTION OF PREFERRED FEATURES

The alignment device of the invention is for retention permanently in the limb. For setting up the limb, the upper and lower parts are connected by a temporary alignment device which provides a mechanical connection that is releaseable to enable adjustments to be made to establish an alignment. The limb is then placed in a jig that preserves the alignment when the temporary alignment device is removed. The temporary alignment device is then replaced by an alignment device according to the invention which adopts the alignment preserved in the jig. The cavity is initially filled with air, and passage means leads through one of the end plates to and from the cavity for introduction of hardenable material therein.

Usually the limb is an artificial leg, the jig is a vertical alignment stand, and the stump socket is worn by a patient during the positional adjustment of the stump socket and the lower limb parts. The method may then comprise the further steps of returning the limb to the jig, removing the temporary alignment device, attaching between the stump socket and the lower parts of the limb a permanent alignment device having an internal cavity permitting said permanent alignment device to deform and then take up an alignment preserved by said jig, filling the cavity with hardenable material, and after the material has hardened removing the limb from the jig.

BRIEF DESCRIPTION OF THE DRAWINGS

An embodiment of the invention will now be described, by way of example only, with reference to the accompanying drawings, in which.

DETAILED DESCRIPTION OF A PREFERRED FORM OF THE INVENTION

Figure 1:
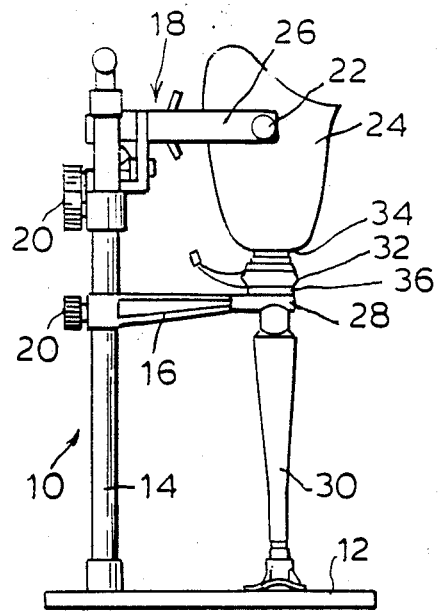
FIG. 1 is a front elevation of an alignment stand for use in the dynamic alignment of an artificial leg for an above-knee amputee.
Figure 2:
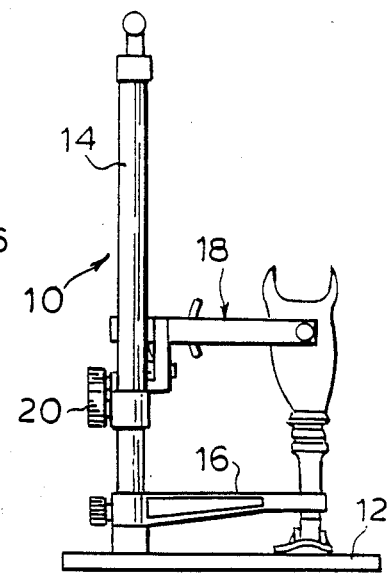
FIG. 2 is an elevation as for FIG. 1 but for a below-knee amputee.

In FIG. 1, an alignment stand 10 has a baseplate 12 and a column 14 carrying a limb support bracket 16 and a socket-supporting gimbal 18 each settable at an appropriate height for an individual patient by clamping screws 20. In an alternative form the alignment stand 10 may be provided without the column 14, the bracket 16 and gimbal 18 being in a track or the like that is wall-mounted. A socket 24 is held in a predetermined datum position in arms 26 of the gimbal 18 by anterior and posterior locating lugs 22 adhered to the socket 24 in a previous static alignment procedure to take account of the load line passing through the socket. The lugs 22 serve to position the socket 24 and will normally be located thereon in a position at right angles to the intended load line. The gimbal 18 provides for independent medial/lateral translation and angulation, anterior/posterior translation and angulation and socket polar rotation without loss of the previous settings. It may also allow calibrations to be recorded. The support bracket 16 has a clamping mechanism 28 at its tip to clamp a shin or ankle portion 30 of a leg prosthesis or, in the case e.g. of a long below-knee or Symes amputation, simply a foot. FIG. 2 shows the alignment stand in use for a below knee amputation and it may be seen that essentially the same principles are employed.

When the dynamic alignment is being set, there is first interposed between the socket 24 and the shin portion 30 a temporary alignment device 32 which has upper and lower plates that dlamp in face to face contact with corresponding formations in a socket base 34 and a knee top 36 respectively. The upper and lower plates are mechanically connected by releaseable mechanical coupling means (not shown) such as jacking screws that permit free universal relative movement of the socket 24 and the shin portion 30 under the control of gimbal 18.

Figure 3:
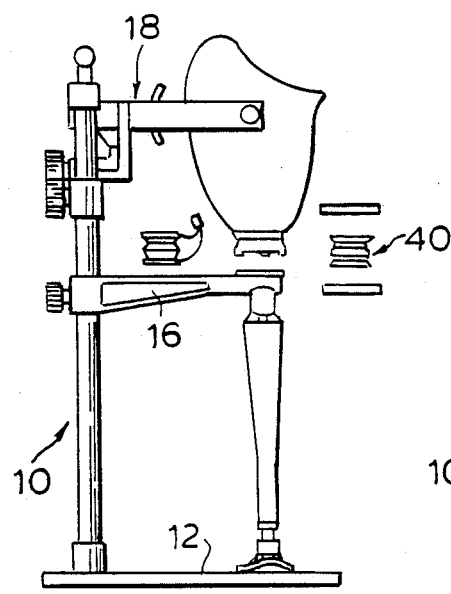
FIG. 3 is an elevation of the alignment stand showing replacement of a temporary alignment device in the limb by a spacer unit to be formed with an intended permanent alignment.
Figure 4:
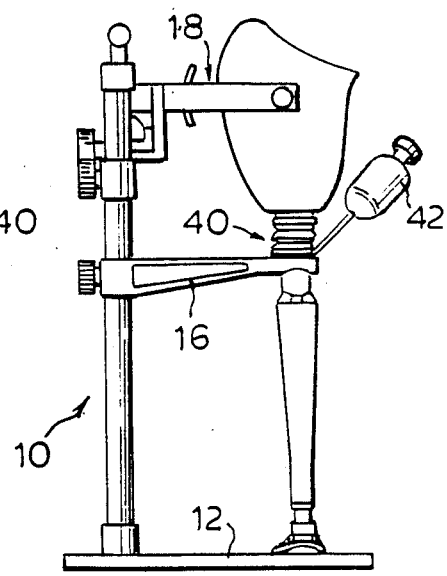
FIG. 4 is an elevation like FIG. 3 showing filling of the spacer unit.

In use, the limb will have been statically aligned and will incorporate the socket 24, the temporary alignment device 32 and the shin part 30 assembled together. The patient, wearing the limb, will first walk with the limb to allow the prosthetist to assess what alignments need to be adjusted. The patient then enters the stand 10, locating the socket lugs 22 in the gimbal 18 and the prosthetist clamps the clamping mechanism 28 onto the shin part 30. The temporary alignment device 32 is then released and the appropriate alignment changes may be effected using gimbal 18, after which the temporary alignment device 32 is clamped to preserve the alignment and the patient walks from the stand to check the new alignment. This procedure is repeated until the prosthetist has determined that the dynamic alignment is satisfactory. When this has been achieved, the leg is removed from the patient and returned to the stand as in FIG. 3. The temporary alignment device 32 is removed and replaced by a permanent alignment device 40 having the same end fittings as the temporary alignment device 32 and which is secured in place by clamping means. The alignment device 40 is "permanent" in the sense that it permanently preserves the dynamic alignment which has been established, but as mentioned below it is removable from the upper and lower parts of the leg if the patient's condition changes and he needs a new alignment. An internal cavity of the permanent alignment device 40 is then filled with hardenable material from a gun 42 as shown in FIG. 4, so that the permanent alignment device 40 becomes rigid and preserves the alignment obtained. The permanent alignment device 40 now provides a definitive alignment, and after the leg has been finished by fitting a cosmesis in place, it is ready for use by the patient. The patient will normally walk on the limb soon after the material in the internal cavity of the permanent alignment device 40 has set in order to confirm the alignment obtained. If he and the prosthetist are satisfied with the alignment the limb can be sent for cosmetic finishing. If the patient needs an alignment change e.g. because of changes in stump volume, the above procedure can simply be repeated after removal of the old alignment device 40 to obtain a new permanent alignment device 40 incorporating the new alignment.

Figure 5:
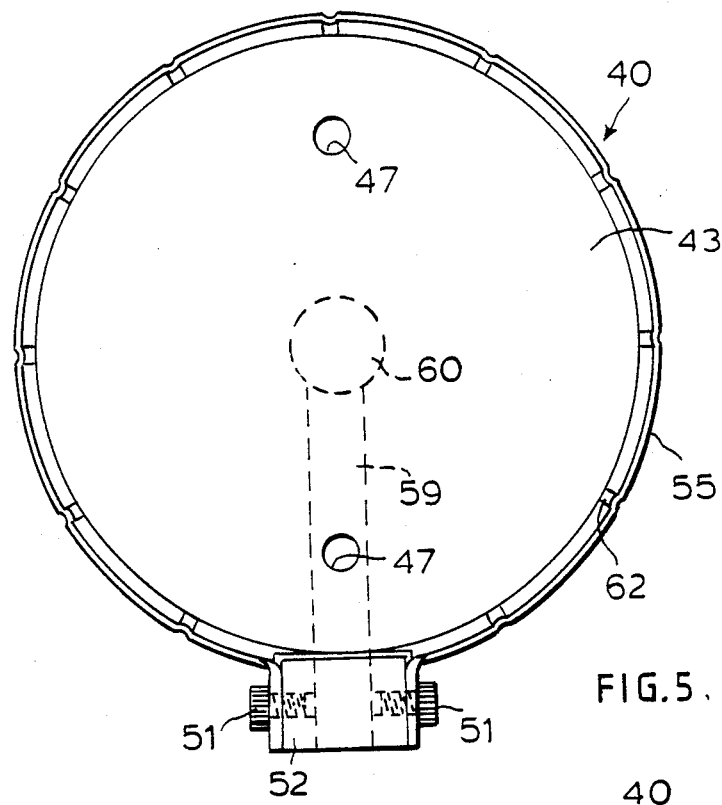
FIGS. 5, 6 and 7 are respectively a plan, and end elevation and a section on the line A—A of a spacer unit according to the invention.
Figure 6:
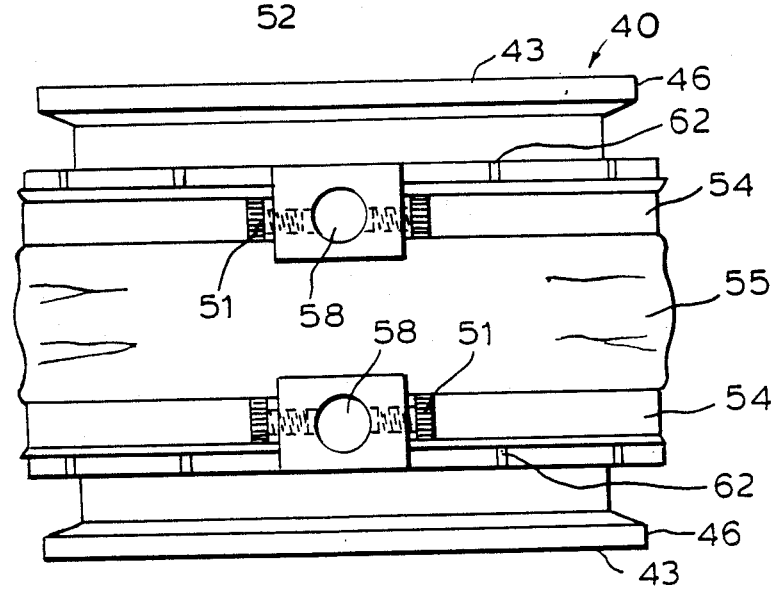
Figure 7:
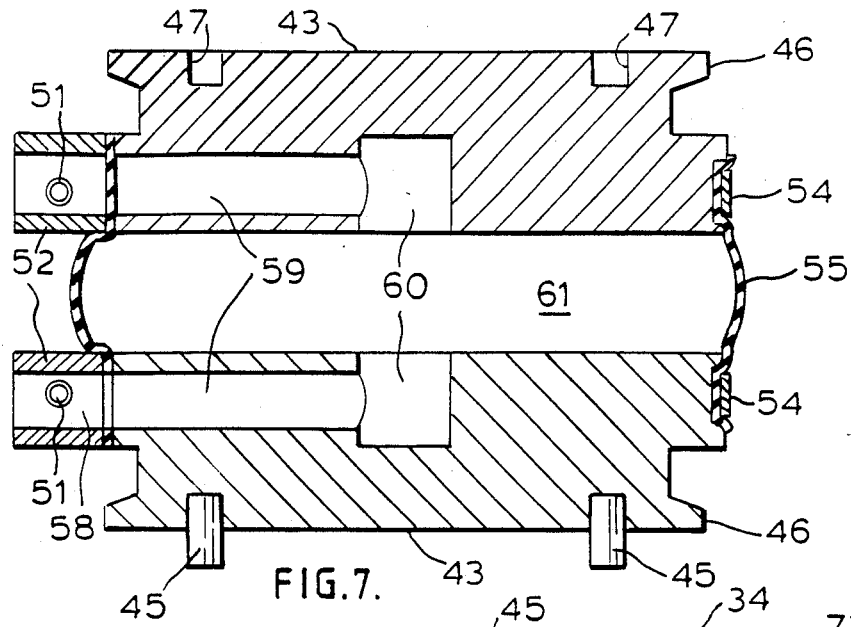

FIGS. 5 to 7 show a permanent alignment device 40 for fitting in place of the temporary alignment device 32 when a satisfactory alignment has been achieved. It comprises upper and lower end plates 43 that are flanged at 46. The upper end plate is formed on its exposed face with sockets 47 to receive anti-rotation pegs depending from the socket base 34. The lower end plate has on its end face depending anti-rotation pegs 45 for reception in sockets formed in knee top 36. It is understood that the temporary alignment device 32 will have corresponding sockets and anti-rotation pegs so as to be interchangeable with the permanent alignment device 40. A flexible sleeve 55 fits between the plates 43 to which it is held by means of clamping bands 54, clamping/filler blocks 52 and clamping screws 51. Passages 58 through the clamping/filler blocks 52 connect with radial passages 59 and axial passages 60 of end plates 43 and lead to an internal cavity 61 of the permanent alignment device 40. The cavity 61 can be filled through the passages 58 with a hardenable liquid composition such as a rapid-setting epoxy resin from gun 42. Air is vented from the internal cavity 61 through breather slots 62 which communicate the cavity 61 with the exterior. Advantageously the side surfaces of the end plates 43 are formed with the breather slots 62 which lead under the flexible sleeve 55 from the internal cavity 61 to the outside to assist air escape from the cavity 61 and prevent formation of gas bubbles in the cavity as it fills with hardenable material. When the hardenable liquid has cured or set, the plates 43 are mechanically linked through the body of hardened liquid in the cavity 61 and are held rigidity in the intended alignment. The limb is then ready for final checking of alignment on the amputee before cosmetic finishing.

Figure 8:
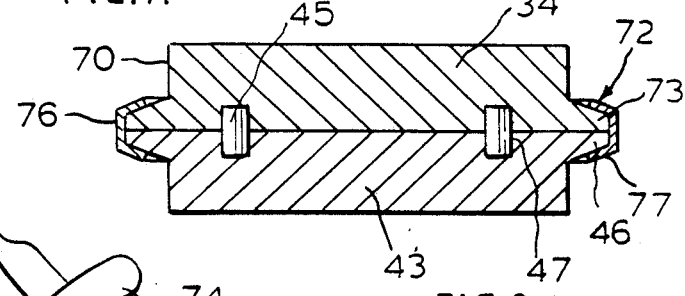
FIG. 8 is a section of one end plate of the spacer unit and an abutting formation of an upper and lower part of the leg showing a clamping unit.
Figure 9:
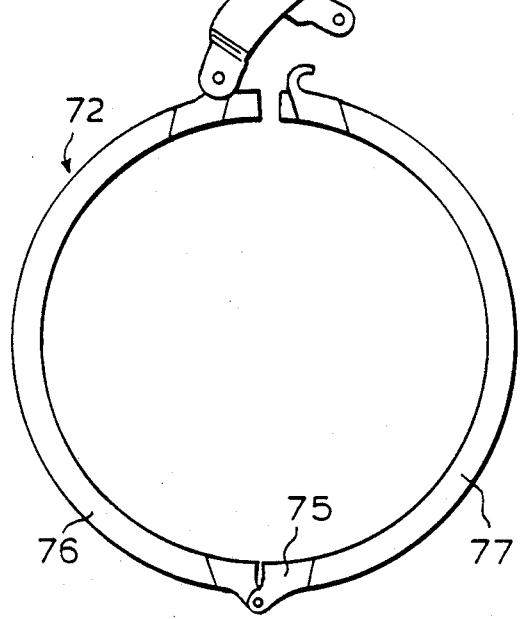
FIG. 9 is a plan of the clamping unit released and removed from the leg.

The temporary alignment device 32 and the permanent alignment device 40 are held in angular and axial position relative to the socket base 34 and knee top 36 as illustrated in FIGS. 8 and 9. An end plate 43, for example, is placed in face-to-face contact with a flanged end 70 of, for example, a socket base 34 and a clamping band 72 of channel section fits over abutting flanges 46,73 and is of complementary section. The band 72 is formed in halves 76, 77 hinged together at 75 and opened or closed to clamp or release the parts 34,43 by means of a toggle action clip 74 located diametrically opposite to the hinge 75. If desired the toggle clip 74 may be replaced by a screw fixing.

We claim:

1. In an artificial limb having upper and lower limb parts, and an alignment device positioned between the upper and lower limb parts, the improvement comprising:

said alignment device having first and second end plates fastened to the upper and lower limb parts, respectively, in predetermined angular and axial position;

flexible sleeve means being fastened between the end plates to define therewith an internal cavity for containing a body of hardenable fluid material; and passage means through which the hardenable fluid material may flow to the internal cavity from the exterior of the alignment device, relative movement between said upper and lower limb parts during alignment thereof being accommodated when the material is in a fluid state, and said hardenable material providing a rigid mechanical link between the first and second end plates when the material is in a hardened state.

2. An artificial limb according to claim 1, wherein: alignment means is provided between the end plates and the respective upper and lower limb parts, said alignment means comprising interengaged sockets and pegs on the end plates and upper and lower limb parts, respectively.

3. An artifical limb according to claim 1, wherein: the ends of an end plate and the adjacent limb part are fastened together in abutting relationship, are both formed with flanged ends, and a releasable clamping band encircles the abutting flanged ends to hold said end plate and said limb part together.

4. An artificial limb according to claim 1, wherein: said flexible sleeve means is fastened to the end plates by clamping band means.

5. An artificial limb according to claim 1, wherein: breather passage means leads from said internal cavity for the outflow of air displaced by the inflow of said hardenable material.

6. An artificial limb according to claim 5, wherein: recesses in the side face of at least one of said end plates define said breather passage means and extend under the flexible sleeve means from the internal cavity to the outside of the alignment device.

7. An artificial limb according to claim 1, wherein: said passage means leads through at least one end plate to the internal cavity.

8. A method for manufacturing an artificial limb, comprising the steps of fitting a temporary mechanical alignment device between a stump socket and lower parts of the limb, releasing a mechanism of the temporary alignment device, adjusting the relative positions of the stump socket and the lower parts in jig means, reclamping the alignment device and removing the limb from the jig means so that the patient can test the limb, returning the limb to the jig means, removing the temporary alignment device, attaching between the stump socket and the lower parts of the limb a permanent alignment device having an internal cavity permitting said permanent alignment device to deform and take up an alignment preserved by said jig, filling the internal cavity with hardenable material, and after the material has hardened removing the limb from the jig.

9. A method according to claim 8, wherein the limb is an artificial leg, the jig means is a vertical alignment stand, and the stump socket is worn by a patient during the positional adjustment of the stump socket and the lower limb parts.

10. A method according to claim 8, wherein the hardenable material is an epoxy resin injected into the internal cavity means of a gun.

11. In an artificial limb having upper and lower limb parts, and an alignment device positioned between the upper and lower limb parts, the improvement comprising:

first and second spaced apart end plates for attachment to respective upper and lower limb parts;
means for fastening each end plate to a respective upper and lower limb part of an artificial limb in predetermined angular and axial position;
flexible sleeve means fastened between the end plates to define therewith an internal cavity for containing a body of hardenable fluid material; and
passage means through which the hardenable fluid material may flow to the internal cavity from the exterior of the device, said fluid material enabling relative movement between the first and second end plates when the material is in a fluid state, and said fluid material providing a rigid mechanical linkage between the end plates when the material is in a hardened state.

12. A device according to claim 11, comprising:
alignment means on said end plates for cooperation with complemental alignment means on upper and lower limb parts of an artificial limb to maintain the end plates in alignment with upper and lower limb parts attached thereto.

13. A device according to claim 11, wherein:
the ends of an end plate and a limb part to which the end plate is to be fastened are both flanged, the flanged ends being engageable in abutting relationship and fastenable together by means of a clamping band encircling the abutting flanged ends.

14. A device according to claim 11, comprising:
breather passage means leading from said internal cavity for the outflow of air displaced by the inflow of said hardenable fluid material.

15. A device according to claim 11, wherein said flexible sleeve means is fastened to the end plates by clamping band means.

16. A device according to claim 14, wherein recesses in the side face of at least one of said end plates define said breather passage means and extend under the flexible sleeve means from the internal cavity to the outside of the device.

17. A device according to claim 11, wherein:
said passage means lead through at least one end plate to the internal cavity.

* * * * *